US00PP22254P2

(12) United States Plant Patent
Hanna et al.

(10) Patent No.: US PP22,254 P2
(45) Date of Patent: Nov. 15, 2011

(54) ORNAMENTAL GRASS 'TIFT-8'

(50) Latin Name: ***Pennisetum purpureum*×[*Pennisetum glaucum*×(*Pennisetum purpureum*×*Pennisetum squamulatum*)]**
Varietal Denomination: Tift 8

(75) Inventors: Wayne William Hanna, Chula, GA (US); S. Kristine Braman, Griffin, GA (US); Brian Matthew Schwartz, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 12/802,937

(22) Filed: Jun. 17, 2010

(51) Int. Cl.
*A01H 5/00* (2006.01)

(52) U.S. Cl. ..... Plt./384

(58) Field of Classification Search ..... Plt./384
See application file for complete search history.

(56) References Cited

U.S. PATENT DOCUMENTS

PP17,728 P3 5/2007 Hanna
2010/0212053 P1 8/2010 Hanna

*Primary Examiner* — Annette Para
(74) *Attorney, Agent, or Firm* — Davis Wright Tremaine LLP

(57) ABSTRACT

The new variety *Pennisetum* 'Tift 8' is provided. The new and distinct variety has high ornamental value; cold tolerance for short periods of time; and relatively long trichomes on the sheath and at the leaf blade edge at the collar. The asexually reproduced variety is reliably propagated vegetatively.

1 Drawing Sheet

Latin name of the genus of the plant claimed: 'Tift 8' is a tri-specific ornamental *Pennisetum* hybrid of the genus and species *Pennisetum purpureum*×*[Pennisetum glaucum*×(*Pennisetum purpureum*×*Pennisetum squamulatum*)].

Variety denomination: The new *Pennisetum* claimed is of the variety denominated 'Tift 8'.

BACKGROUND OF THE INVENTION

The present invention relates to a new and distinct cultivar of *Pennisetum* and herein referred to as 'Tift 8'.

The new *Pennisetum* is a product of a planned breeding program conducted in Tifton, Ga. The objective of the *Pennisetum* breeding program is to create new plant cultivars with improved commercial qualities. This cultivar is commercially important for its superior ornamental value. These and other qualities are enumerated herein.

Pedigree and history: In 2003, red tetraploid (2n=4x=28) pearl millet (unpatented *Pennisetum glaucum*; designated '04-94') was crossed with SC 1125-2[a Merkeron napiergrass (unpatented *Pennisetum purpureum;* 2n=4x=28) that had been crossed with PS 262 (unpatented *Pennisetum squamulatum;* 2n=8x=56)]. One vigorous plant from the SC 1125-2/PS 262 cross, designated '04-26-1', was selected in 2004. In 2004, 'Princess' napiergrass (U.S. Plant Pat. No. 17,728; 2n=4x=28, female parent) was pollinated with '04-26-1' (unpatented; male parent). The new variety 'Tift 8' was the eighth plant selected in 2005 from the 2004 cross. The new variety 'Tift 8' has been tested since 2005.

Asexual reproduction of the new variety *Pennisetum* 'Tift 8' by vegetative propagation (single stem propagules) in a controlled environment in Tifton, Blairsville and Griffin, Ga. since 2006, has shown that the unique features of this new *Pennisetum* hybrid are stable and reproduced true to type in successive generations.

SUMMARY OF THE INVENTION

The following traits have been repeatedly observed and represent the characteristics of a new variety of *Pennisetum*, 'Tift 8'. The new variety 'Tift 8' has not been observed under all possible environmental conditions. The phenotype may vary somewhat with variations in, for example, temperature, day-length, light intensity, soil types, and water and fertility levels without, however, any variance in genotype.

Throughout this specification, color names beginning with a small letter signify that the name of that color, as used in common speech, is aptly descriptive. Color names beginning with a capital letter designate values based upon The R.H.S. Colour Chart 5$^{th}$ edition published by The Royal Horticultural Society, London, England.

The following traits have been repeatedly observed in Tifton and Griffin, Ga., and are determined to be the unique characteristics of the new variety 'Tift 8':

1. 'Tift 8' reaches a height of about 1.8 meters, and a spread of about 1.6 meters.
2. 'Tift 8' exhibits a vigorous growth habit.
3. 'Tift 8' is pollen and seed sterile.
4. 'Tift 8' is a tender perennial in climates colder than USDA Zone 8a.

The new variety *Pennisetum* 'Tift 8' can be compared to its parents, 'Princess' and '04-26-01', and its sister hybrid 'Tift 17', described in co-pending U.S. Plant patent application Ser. No. 12/378,547, filed on Feb. 17, 2009.

Plants of the new *Pennisetum* differ from its parent 'Princess' in the following characteristics:

1. The new variety 'Tift 8' is taller than 'Princess'.
2. The canopy diameter of the new variety 'Tift 8' is wider compared to the canopy diameter of 'Princess'.

Plants of the new *Pennisetum* differ from its male parent '04-26-1' in the following characteristics:

1. The new variety 'Tift 8' is slightly different from '04-26-1' in adaxial leaf color. The new variety 'Tift 8' is about Greyed-purple RHS 187A, whereas '04-26-1' is about mottled Greyed-purple RHS 183B.
2. The new variety 'Tift 8' has a different midrib color. The new variety 'Tift 8' is about Greyed-purple RHS 187A, while '04-26-1' is about Red-purple RHS 61C:

Plants of the new *Pennisetum* differ from its sister hybrid 'Tift 17' in the following characteristics:

1. The new variety 'Tift 8' is significantly taller than 'Tift 17.'
2. Culm-leaf angle is significantly smaller for 'Tift 8' compared to 'Tift 17.'

The following observations, measurements and values describe plants grown in Tifton, Blairsville, or Griffin, Ga., or both. In Tables 1-9, the least significant difference (LSD) is set at P≦0.05 probability level. Growth days were included in ratings. Plants were spaced at 2 meter centers. All data are from plants established as single stem propagules in mid-May, and rated in September through October, except the data labeled "Test 1," from 2007 and 2009, in which the plants had been over-wintered at Tifton, Ga.

The new variety 'Tift 8' was significantly taller than 'Tift 17' in three of four tests at Tifton, Ga. and in one test at Griffin, Ga. (Table 1). The canopy diameter and base diameter at ground level were observed to be similar between 'Tift 8' and 'Tift 17' (Tables 2 and 3). Leaf width differences between 'Tift 8' and 'Tift 17' were significant in two of four tests (Table 4). No significant differences were measured between these two cultivars for leaf length (Table 5). Culm-leaf angle was significantly smaller for 'Tift 8' compared to 'Tift 17' (Table 6). 'Tift 8' had significantly more leaves per culm than 'Tift 17' (Table 6). On Dec. 21, 2009, inflorescences were exserted on 'Tift 8', but not on 'Tift 17' (completely vegetative) in three different tests (Table 6). 'Tift 17' produced significantly more culms per plant than 'Tift 8' in only one of five tests (Table 7).

TABLE 1

Plant heights of two ornamental *Pennisetum* grasses planted at three locations for three years in Georgia.

| | Tifton | | | | Blairsville | Griffin | |
|---|---|---|---|---|---|---|---|
| | 2006 | 2007 | 2009 | 2007 | 2006 | 2007 | 2006 |
| | Growth days | | | | | | |
| | 158 d Test 1 | 188 d Test 1 | 189 d Test 1 | 151 d Test 2 | 138 d | 123 d | 165 d |
| 'Tift 8' | 132 | 154 | 184 | 107 | 73 | 132 | 156 |
| 'Tift 17' | 115 | 126 | 148 | 99 | 72 | 140 | 117 |
| LSD | 19 | 18 | 25 | 4 | 31 | 41 | 19 |

In Table 1, plant heights were measured from ground level to the top of the canopy. All height measurements are in cm. Plant height measured from ground level to top of plant canopy. At Tifton, Ga., 'Tift 8' and 'Tift 17' were planted on May 11, 2006, with measurements taken on Sep. 20, 2006, Sep. 17, 2007, and Oct. 6, 2009 ("Test 1"). The plants originally planted in 2006 survived the winters of 2006/2007, 2007/2008, and 2008/2009, in the field. "Test 2" represents a planting of 'Tift 8' and 'Tift 17' that occurred on Apr. 19, 2007, with measurements made on Sep. 17, 2007. At Blairesville, Ga., 'Tift 8' was planted on Jun. 2, 2006 and May 27, 2007, with measurements made on Oct. 18, 2006 and Sep. 27, 2007, respectively. At Griffin, Ga., 'Tift 8' was planted on May 6, 2006, with measurements taken on Oct. 18, 2006.

TABLE 2

Canopy diameter of individual plants of two ornamental *Pennisetum* grasses planted at three locations for two years in Georgia. Plants were spaced on two meter centers.

| | Tifton | | | Blairsville | | Griffin |
|---|---|---|---|---|---|---|
| | 2006 | 2007 | 2007 | 2006 | 2007 | 2006 |
| | Growth days | | | | | |
| | 158 d Test 1 | 188 d Test 1 | 151 d Test 2 | 138 d | 123 d | 165 d |
| 'Tift 8' | 143 | 166 | 129 | 133 | 147 | 162 |
| 'Tift 17' | 143 | 160 | 133 | 141 | 135 | 154 |
| LSD | 17 | 23 | 4 | 24 | 40 | 18 |

Plant canopy measurements, as shown in Table 2, represent the average of the diameters measured at the estimated widest and narrowest portions of a single plant canopy. Measurements are in cm. At Tifton, Ga., 'Tift 8' was planted on May 11, 2006, with measurements taken on Sep. 20, 2006, Sep. 17, 2007 ("Test 1"). The plants originally planted in 2006 survived the 2006/2007 winter in the field. "Test 2" represents a planting of 'Tift 8' that occurred on Apr. 19, 2007, with measurements made on Sep. 17, 2007. At Blairesville, Ga., 'Tift 8' was planted on Jun. 2, 2006 and May 27, 2007, with measurements made on Oct. 18, 2006 and Sep. 27, 2007, respectively. At Griffin, Ga., 'Tift 8' was planted on May 6, 2006, with measurements taken on Oct. 18, 2006.

TABLE 3

Base diameter at ground level of individual plants of two ornamental *Pennisetum* grasses planted at three locations for two years in Georgia.

| | Tifton | | | Blairsville |
|---|---|---|---|---|
| | 2006 | 2007 | 2007 | 2007 |
| | Growth days | | | |
| | 158 d Test 1 | 188 d Test 1 | 151 d Test 2 | 123 d |
| 'Tift 8' | 48 | 44 | 22 | 37 |
| 'Tift 17' | 49 | 47 | 23 | 32 |
| LSD | 3 | 10 | 3 | 9 |

Base diameter is the diameter of the base of a single plant. Measurements are in cm. At Tifton, Ga., 'Tift 8' was planted on May 11, 2006, with measurements taken on Sep. 20, 2006, Sep. 17, 2007 ("Test 1"). The plants originally planted in 2006 survived the 2006/2007 winter in the field. "Test 2" represents a planting of 'Tift 8' that occurred on Apr. 19, 2007, with measurements made on Sep. 17, 2007. At Blairesville, Ga., 'Tift 8' was planted on May 27, 2007, with measurements made on Sep. 27, 2007.

TABLE 4

Leaf width of individual plants of two ornamental *Pennisetum* grasses planted at three locations for two years in Georgia.

| | Tifton | | Blairsville | Griffin |
|---|---|---|---|---|
| | 2006 | 2007 | 2006 | 2006 |
| | Growth days | | | |
| | 158 d Test 1 | 151 d Test 2 | 138 d | 165 d |
| 'Tift 8' | 3 | 30 | 30 | 33 |
| 'Tift 17' | 29 | 30 | 27 | 38 |
| LSD | 4 | 2 | 11 | 5 |

The leaf width was measured in the center of the latest fully extended leaf. At Tifton, Ga., 'Tift 8' was planted on May 11, 2006, with measurements taken on Sep. 20, 2006 ("Test 1"). "Test 2" represents a planting of 'Tift 8' that occurred on Apr. 19, 2007, with measurements made on Sep. 17, 2007. At Blairesville, Ga., 'Tift 8' was planted on Jun. 2, 2006, with measurements made on Oct. 18, 2006. At Griffin, Ga., 'Tift 8' was planted on May 6, 2006, with measurements taken on Oct. 18, 2006.

TABLE 5

Leaf length on individual plants of two ornamental *Pennisetum* grasses at three locations for two years in Georgia.

| | Tifton | | Blairsville | Griffin |
|---|---|---|---|---|
| | 2006 | 2007 | 2006 | 2006 |
| | Growth days | | | |
| | 158 d Test 1 | 151 d Test 2 | 138 d | 165 d |
| 'Tift 8' | 63 | 56 | 84 | 78 |
| 'Tift 17' | 68 | 61 | 83 | 70 |
| LSD | 11 | 5 | 12 | 11 |

The leaf length was measured from the leaf collar to the leaf tip of the latest fully extended leaf. At Tifton, Ga., 'Tift 8' was planted on May 11, 2006, with measurements taken on Sep. 20, 2006 ("Test 1"). "Test 2" represents a planting of 'Tift 8' and 'Tift 17' that occurred on Apr. 19, 2007, with measurements made on Sep. 17, 2007. At Blairesville, Ga., 'Tift 8' and 'Tift 17' were planted on Jun. 2, 2006, with measurements made on Oct. 18, 2006. At Griffin, Ga., 'Tift 8' and 'Tift 17' were planted on May 6, 2006, with measurements taken on Oct. 18, 2006.

TABLE 6

Leaf angle, leaf number, and heading characteristics of individual plants (spaced on 2 meter centers) of two ornamental *Pennisetum* grasses planted at Tifton, Georgia.

| | Culm-Leaf | Number | Inflorescence Exsertion | | |
|---|---|---|---|---|---|
| Entry | Angle 2008 | Leaves/Culm 2008 | 2006 Test 1 | 2009 Test 2 | 2009 Nursery |
| 'Tift 8' | 19 | 11.3 | 4.3 | 2.6 | 3.9 ± 0.3 |
| 'Tift 17' | 27 | 9.6 | 1.0 | 1.0 | 1.0 ± 0.0 |
| LSD | 4.5 | 1.3 | 0.2 | 0.5 | — |

The leaf angle and the number of fully extended leaves per culm were measured on plants planted on May 12, 2008, with the measurements occurring on Oct. 10, 2008. The measured leaf angle was the angle observed between the adaxial leaf surface and the culm at the leaf collar on the last fully extended leaf.

The reported inflorescence exsertion data represents the translation of the percentages of culms with fully exserted inflorescences into a numerical score. That is, a score of 1 is assigned to a completely vegetative plant, 2 represents 1-10% of culms with fully exserted inflorescences, 3 (11-20% of culms with fully exserted inflorescences), 4 (31-40%), 5 (41-50%), 6 (51-60%), 7 (61-70%), 8 (71-80%), and 9 (>80%).

'Tift 8' and 'Tift 17' were planted on May 11, 2006 ("Test 1"). These plants survived the winters of 2006/2007, 2007/2008, and 2008/2009, at Tifton, Ga. The plants of "Test 2" were planted on May 9, 2009, while the plants termed "Nursery" 2009 were planted on May 9, 2009. All the ratings were made on Dec. 21, 2009.

TABLE 7

Total number of culms on individual plants (spaced on two meter centers) of two ornamental *Pennisetum* grasses planted at three locations for two years in Georgia.

| | Tifton | | | Blairsville | Griffin |
|---|---|---|---|---|---|
| | 2006 | 2007 | 2007 | 2006 | 2006 |
| | Growth days | | | | |
| | 158 d Test 1 | 188 d Test 1 | 151 d Test 2 | 138 d | 165 d |
| 'Tift 8' | 38 | 58 | 25 | 47 | 43 |
| 'Tift 17' | 52 | 61 | 27 | 65 | 38 |
| LSD | 21 | 28 | 3 | 16 | 15 |

At Tifton, Ga., 'Tift 8' and 'Tift 17' were planted on May 11, 2006, with measurements taken on Sep. 20, 2006, Sep. 17, 2007, and Oct. 6, 2009 ("Test 1"). The plants originally planted in 2006 survived the winters of 2006/2007, 2007/2008, and 2008/2009, in the field. "Test 2" represents a planting of 'Tift 8' and 'Tift 17' that occurred on Apr. 19, 2007, with measurements made on Sep. 17, 2007. At Blairesville, Ga., 'Tift 8' and 'Tift 17' were planted on June 2, with measurements made on Oct. 18, 2006. At Griffin, Ga., 'Tift 8' and 'Tift 17' were planted on May 6, 2006, with measurements taken on Oct. 18, 2006.

TABLE 8

Color ratings on individual plants (spaced on two meter centers) of two ornamental *Pennisetum* grasses planted at three locations for up to three years in Georgia.

| | Tifton | | Blairsville | | | Griffin |
|---|---|---|---|---|---|---|
| | 2006 | 2009 | 2007 | 2007 | 2009 | 2006 |
| | Growth days | | | | | |
| | 158 d Test 1 | 181 d Test 1 | 151 d Test 2 | 123 d | 163 d | 141 d |
| 'Tift 8' | 8.3 | 8.6 | 7.1 | 7.5 | 8.3 | 9.0 |
| 'Tift 17' | 7.8 | 7.6 | 7.0 | 7.0 | 7.3 | 8.0 |
| LSD | 0.7 | 0.6 | 0.5 | 0.8 | 0.7 | 0.5 |

At Tifton, Ga., 'Tift 8' and 'Tift 17' were planted on May 11, 2006, with measurements taken on Sep. 20, 2006 and Oct. 6, 2009 ("Test 1"). "Test 2" represents a planting of 'Tift 8' and 'Tift 17' that occurred on Apr. 19, 2007, with measurements made on Sep. 17, 2007. Color in Test 2 was rated on young propagules in the greenhouse on Jan. 28, 2007 before the plants were transplanted to the field. At Blairesville, Ga., 'Tift 8' and 'Tift 17' were planted on May 27, 2007 and Apr. 28, 2009, with measurements taken on Sep. 18 and 27, 2009. At Griffin, Ga., 'Tift 8' and 'Tift 17' were planted on May 14, 2009, with measurements taken on Oct. 2, 2009.

TABLE 9

*Helminthosporium* leaf spot ratings on two ornamental *Pennisetum* grasses planted at three locations for up to two years.

| | Tifton | Griffin | Blairsville | |
|---|---|---|---|---|
| | 2008<br>153 d<br>Oct. 27 | 2006<br>165 d<br>Oct. 18 | 2006<br>138 d<br>Oct. 18 | 2007<br>123 d<br>Sep. 27 |
| 'Tift 8' | 1.0 | 1.0 | 1.0 | 1.0 |
| 'Tift 17' | 1.0 | 1.0 | 1.0 | 1.0 |
| LSD | 0.2 | 1.0 | 0.6 | 0.5 |

Disease ratings in Table 9 are defined as follows: 1=No disease, 2=1-20%, 3=20-40%, 4=41-60%, 5=>60% leaves infected. Symptoms occur in the field during late August and September. At Tifton, Ga., 'Tift 8' and 'Tift 17' were planted on May 12, 2008, with measurements taken on Oct. 10, 2008 ("Test 1"). At Blairesville, Ga., 'Tift 8' and 'Tift 17' were planted on Jun. 2, 2006 and May 27, 2007, with measurements taken on Oct. 18, 2006 and Sep. 27, 2007, respectively. At Griffin, Ga., 'Tift 8' and 'Tift 17' were planted on May 6, 2006, with measurements taken on Oct. 18, 2006.

TABLE 10

Summary of morphological characteristics of two *Pennisetum* grasses.

| Trait | 'Tift 17' | 'Tift 8' |
|---|---|---|
| Mature plant height | 72-148 cm | 73-184 cm |
| Diameter of plant canopy | 133-160 cm | 133-162 cm |
| Diameter of base | 22-48 cm | 23-49 cm |
| Leaf width | 30-33 mm | 27-38 mm |
| Leaf length | 61-83 cm | 56-84 cm |
| Adaxial leaf surface trichomes | None | Infrequent, less than 0.1 mm |
| Abaxial leaf surface trichomes | None | None |
| Leaf blade margin trichome length | <0.1 m | Infrequent, less than 0.1 mm |
| Leaf collar trichome length | 3 mm | Prominent, 2 mm |
| Leaf blade edge at collar Trichome | 6 mm long for 6 mm from collar | 4 mm long for 11 mm from collar |
| Sheath trichomes | 2 mm long for 2 cm from collar | None |
| Number of tillers | 38-65, decreasing with drought | |
| Adaxial leaf color | Greyed-purple 187D | Greyed-purple 187A |
| Abaxial leaf color | Greyed-purple 187D | Greyed-purple 187A |
| Midrib color | Greyed-purple 187D | Greyed-purple 187A |
| Inflorescence on Oct, 20, 2008 | None | None |
| Inflorescences on Dec. 21, 2009 | Yes | None |
| Number of culms on mature plants | 27-65 | 25-58 |
| *Helminthosporium* leaf spot on mature plants | None | None |

In summary, 'Tift 8' is similar to 'Tift 17' in canopy diameter, plant base diameter, leaf length and width, total number of culms per plant, and disease resistance. 'Tift 8' is taller, has a smaller culm-leaf angle at the collar, produces more leaves per culm, and produces exserted inflorescence at daylength of approximately 10.5 h or less. 'Tift 8' has more attractive color than 'Tift 17'.

BRIEF DESCRIPTION OF THE FIGURES

The accompanying colored photographs illustrate the overall appearance and distinct characteristics of the new variety of *Pennisetum* 'Tift 8'. The colors in the photographs are as close as possible with the photographic and printing technology utilized.

BOTANICAL DESCRIPTION

Figure 1:
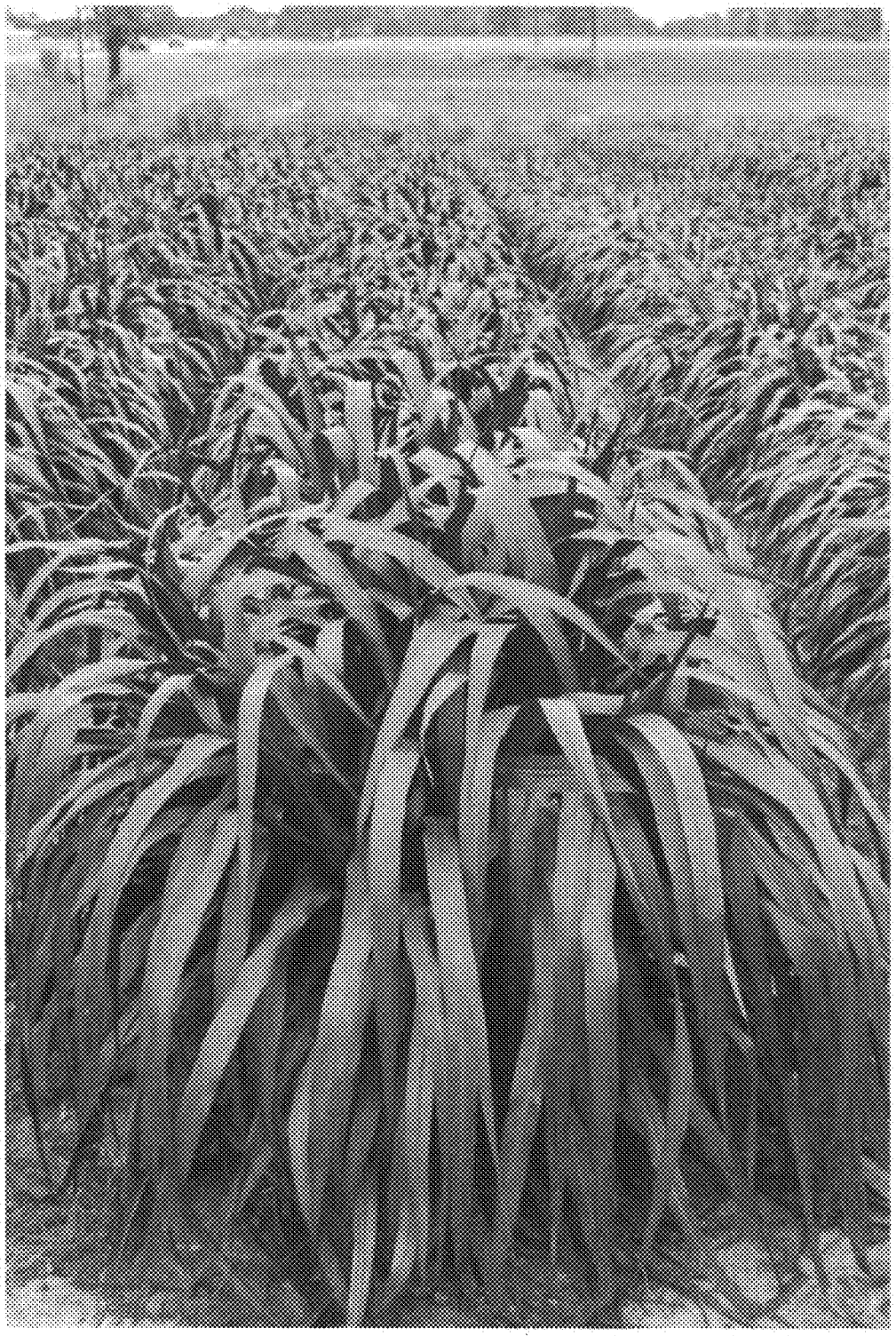
FIG. 1 is a photograph of the new variety *Pennisetum* 'Tift 8'.

The new variety 'Tift 8' is a perennial at Tifton, Ga. (USDA Zone 8a). The new variety 'Tift 8' survived at approximately −7° C. for one night and 13 nights below 0° C. in the field during the 2008/2009 winter at Tifton, and 45 days below 0° C. and a low temperature of −10° C. during the 200/2009 winter at Griffin (USDA Zone 7b). It has not survived the winter temperatures (lows of −13° C. and −15° C. in the 2006/2007 and 2007/2008, respectively) in the mountains of Blairsville, Ga. (USDA Zone 6b). Because of its vigor, it can effectively be used as an annual where it will not survive freezing temperatures in the winter.

All data are from plants established as single stem propagules in mid-May, and rated in September through October, except the 2007 and 2009 Test 1 data are from plants that over-wintered at Tifton. Plants were spaced at 2 meter centers.

Plant:

*Mature plant height.*—Approximately 73-184 cm.

*Diameter of plant canopy.*—Approximately 133-162 cm.

*Diameter of base.*—Approximately 22-49 cm.

Leaf:

*Leaf width.*—Approximately 27-38 mm.

*Leaf length.*—Approximately 56-84 mm.

*Adaxial leaf surface trichomes.*—Infrequent, less than 0.1 mm.

*Abaxial leaf surface trichomes.*—None.

*Leaf blade margin trichome length.*—Infrequent, less than 0.1 mm.

*Leaf collar trichome length.*—Prominent, 2 mm.

*Leaf blade edge at collar trichome.*—Approximately 4 mm long for about 11 mm from collar.

*Sheath trichomes.*—None.

*Number of tillers.*—Approximately 38-65, decreasing with drought.

*Adaxial leaf color.*—About Greyed-purple RHS 187A.

*Abaxial leaf color.*—About Greyed-purple RHS 187A.

*Midrib color.*—About Greyed-purple RHS 187A.

*Helminthosporium leaf spot on mature plants.*—None.

*Inflorescence.*—No pollen or seed has been observed on 'Tift 8' plants flowering in the green house during the winter (short days).

Culm:

*Number of culms on mature plants.*—Approximately 25-58.

What is claimed is:

1. A new and distinct variety of the *Pennisetum* plant named 'Tift 8', substantially as illustrated and described herein.

* * * * *